United States Patent [19]

Walker et al.

[11] 4,412,955

[45] Nov. 1, 1983

[54] PREPARATION OF CORTICOIDS FROM 17-KETO STEROIDS

[75] Inventors: Jerry A. Walker, Oshtemo Township, Kalamazoo County; Edward J. Hessler, Kalamazoo, both of Mich.

[73] Assignee: The Upjohn Company, Kalamazoo, Mich.

[21] Appl. No.: 378,938

[22] Filed: May 17, 1982

Related U.S. Application Data

[62] Division of Ser. No. 264,593, May 18, 1981, Pat. No. 4,357,279.

[51] Int. Cl.³ ............................................. C07J 7/00
[52] U.S. Cl. ........................... 260/397.45; 260/239.5; 260/397.5
[58] Field of Search .................................... 260/397.45

[56] References Cited

U.S. PATENT DOCUMENTS

4,041,055  8/1977  Shephard et al. ................. 260/397.3
4,357,279  11/1982  Walker et al. .................... 260/397.45

OTHER PUBLICATIONS

J. Am. Chem. Soc. 86, 3840 (1964).
J. Org. Chem. 35, 2831 (1970).

*Primary Examiner*—Elbert L. Roberts
*Attorney, Agent, or Firm*—Bruce Stein

[57] ABSTRACT

Disclosed is a 20,21-dihalo steroid (VII) and a steroidal sulfoxide (VIII) as well as processes to produce them. The 20,21-dihalo steroid (VII) and sulfoxide (VIII) are intermediates useful in the preparation of pharmaceutically useful corticoids.

22 Claims, No Drawings

PREPARATION OF CORTICOIDS FROM 17-KETO STEROIDS

This is a division of application Ser. No. 264,593 filed May 18, 1981 now U.S. Pat. No. 4,357,279.

The present invention relates to intermediates and processes for preparation of those intermediates useful in the preparation of pharmaceutically useful corticoids for which the essential material constituting a disclosure thereof is incorporated here by reference from divisional U.S. patent application Ser. No. 264,593, filed May 18, 1981, now U.S. Pat. No. 4,357,279.

We claim:

1. A 20,21-dihalo steroid of the formula

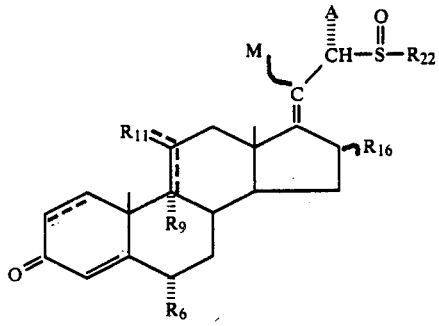

where A is a fluorine, chlorine or bromine atom; M is a fluorine, chlorine or bromine atom; $R_6$ is a hydrogen or fluorine atom or methyl group; $R_9$ is a hydrogen or fluorine atom, hydroxyl group, $-OSi(R)_3$ or nothing; $R_{11}$ is (H), (H,H), (H, $\beta-OSi(R)_3$, or (O); $R_{16}$ is a hydrogen atom or methyl group; $R_{22}$ is alkyl of 1 thru 5 carbon atoms, trichloromethyl, phenyl, phenyl substituted with 1-4 carbon atoms or substituted with 1 thru 3 nitro or trifluoromethyl groups, aralkyl of 7 thru 12 carbon atoms or $-N-(R_{122})_2$ or phthalimide; ~ indicates the attached group can be in either the $\alpha$ or $\beta$ configuration; .... is a single or double bond.

2. A 20,21-dihalo steroid according to claim 1 wherein A is a chlorine atom.

3. A 20,21-dihalo steroid according to claim 2 where A and M are both a chlorine atom.

4. A 20,21-dihalo steroid according to claim 1 where $R_{22}$ is phenyl.

5. A 20,21-dihalo steroid of formula (VII) according to claim 1 where $R_6$ and $R_{16}$ are hydrogen atoms, where $R_9$ is nothing and $R_{11}$ is [H] which gives a $\Delta^{9,11}$ functionality in the C ring.

6. A 20,21-dihalo steroid according to claim 5 which is 20,21-dichloro-21-(phenylsulfinyl)pregna-4,9(11),17(20)-trien-3-one.

7. A sulfoxide of the formula

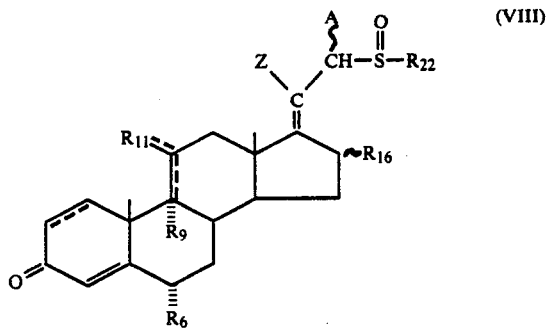

where Z is $-OR_{20}$ or $SR_{20}$; and where A, $R_6$, $R_9$, $R_{11}$, $R_{16}$, $R_{22}$, ~ and .... are defined in claim 1.

8. A sulfoxide according to claim 7 where A is a chlorine atom.

9. A sulfoxide according to claim 7 where Z is methoxy or phenoxy.

10. A sulfoxide according to claim 7 where $R_{22}$ is phenyl.

11. A sulfoxide of formula (VIII) according to claim 7 where $R_6$ and $R_{16}$ are hydrogen atoms, where $R_9$ is nothing and $R_{11}$ is [H] which gives a $\Delta^{9,11}$ functionality in the C ring.

12. A sulfoxide according to claim 7 which is 21-chloro-20-methoxy-21-(phenylsulfinyl)pregna-4,9(11),17(20)-trien-3-one.

13. A process for the preparation of a 20,21-dihalo steroid of the formula

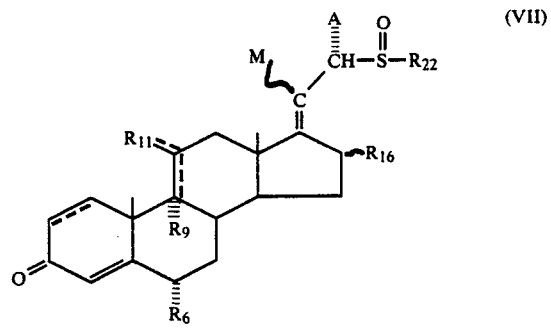

which comprises (1) contacting a C21-steroid of the formula

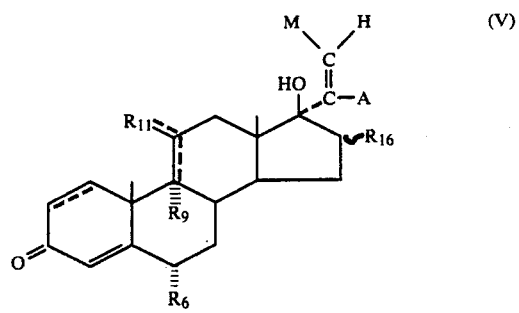

with a sulfenylating agent of the formula $R_{22}-S-X$ (VI), where A, M, $R_6$, $R_9$, $R_{11}$, $R_{16}$, $R_{22}$, ~ and .... are defined in claim 1 and where X is a chlorine or bromine atom, phenylsulfone, phthalimide or imidazole group.

14. A process according to claim 13, where for the 20,21-dihalo steroid (VII), $R_6$ and $R_{16}$ are hydrogen atoms, were $R_9$ is nothing and $R_{11}$ is [H] which gives a $\Delta^{9,11}$ functionality in the C ring.

15. A process according to claim 13 where for the sulfenylating agent, $R_{22}$—S—X, X is a chlorine or bromine atom, and $R_{22}$ is a phenyl group.

16. A process according to claim 13 where the temperature range for the sulfenylation reaction is from about $-80°$ to about $25°$.

17. A process for the preparation of a sulfoxide of the formula

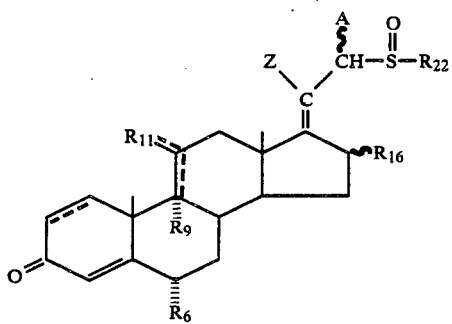

which comprises contacting a 20,21-dihalo steroid of the formula

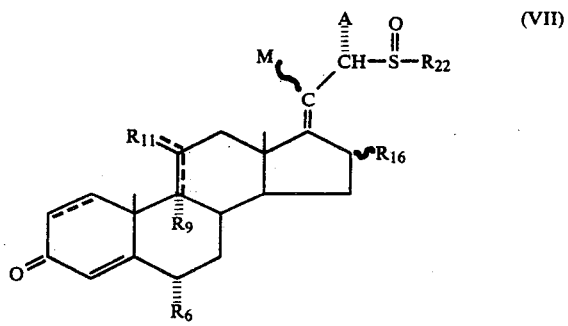

with an alkoxide or mercaptide of the formula $OR_{20}^\ominus$ or $SR_{20}^\ominus$, respectively, where A, M, $R_6$, $R_9$, $R_{11}$, $R_{16}$, $R_{22}$, ∼ and .... are defined in claim 1; and where Z is defined in claim 7, and where $R_{20}$ is alkyl of 1 thru 4 carbon atoms or phenyl.

18. A process according to claim 17, where for the 21-halo steroid (VIII), $R_6$ and $R_{16}$ are hydrogen atoms, where $R_9$ is nothing and $R_{11}$ is [H] which gives a $\Delta^{9,11}$ functionality in the C ring.

19. A process according to claim 17, where the base is an alkoxide.

20. A process according to claim 19, where the alkoxide is methoxide or phenoxide.

21. A process according to claim 17, where the reaction with base is performed in a polar solvent.

22. A process according to claim 17, where 1.0 equivalents of base are used.

* * * * *

UNITED STATES PATENT OFFICE
CERTIFICATE OF CORRECTION

Patent No. 4,412,955                        Dated  November 1, 1983

Inventor(s) Jerry A. Walker et al.

It is certified that error appears in the above-identified patent and that said Letters Patent are hereby corrected as shown below:

Column 1, line 25; column 2, line 40; and column 4, line 5, in formula (VII) the $C_{17}$ side chain should appear as follows:

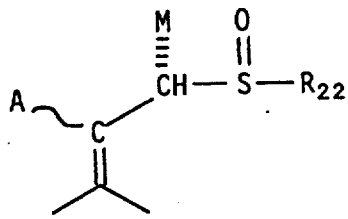

Column 2, line 5; and column 3, line 25, in formula (VIII) the $C_{17}$ side chain should appear as follows:

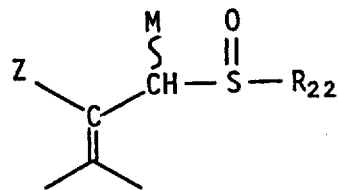

Column 2, line 15, the "A" should be an --M--.

Signed and Sealed this

Ninth Day of October 1984

[SEAL]

Attest:

GERALD J. MOSSINGHOFF

Attesting Officer        Commissioner of Patents and Trademarks